United States Patent
Yoshiike

(10) Patent No.: US 10,478,511 B2
(45) Date of Patent: Nov. 19, 2019

(54) THERAPEUTIC AGENT FOR TAUOPATHY AND METHOD FOR SCREENING THEREOF

(71) Applicant: National Center for Geriatrics and Gerontology, Obu-shi, Aichi (JP)

(72) Inventor: Yuji Yoshiike, Obu (JP)

(73) Assignee: National Center for Geriatrics and Gerontology, Obu-shi (JP)

( * ) Notice: Subject to any disclaimer, the term of this patent is extended or adjusted under 35 U.S.C. 154(b) by 0 days.

(21) Appl. No.: 15/655,997

(22) Filed: Jul. 21, 2017

(65) Prior Publication Data

US 2017/0319716 A1 Nov. 9, 2017

Related U.S. Application Data

(63) Continuation of application No. 14/919,241, filed on Oct. 21, 2015, now abandoned.

(30) Foreign Application Priority Data

Oct. 22, 2014 (JP) ................................ 2014-215409

(51) Int. Cl.
*A61K 49/00* (2006.01)
*A61K 31/5415* (2006.01)
*C09B 11/08* (2006.01)
*C09B 57/00* (2006.01)
*A61K 31/352* (2006.01)

(52) U.S. Cl.
CPC ........ *A61K 49/0008* (2013.01); *A61K 31/352* (2013.01); *A61K 31/5415* (2013.01); *C09B 11/08* (2013.01); *C09B 57/00* (2013.01)

(58) Field of Classification Search
None
See application file for complete search history.

(56) References Cited

U.S. PATENT DOCUMENTS

| | | |
|---|---|---|
| 2002/0168687 A1 | 11/2002 | Wischik et al. |
| 2003/0181389 A1 | 9/2003 | Wuelfert et al. |
| 2005/0108779 A1 | 5/2005 | Lowe et al. |
| 2011/0111072 A1 | 5/2011 | Pasinetti et al. |

FOREIGN PATENT DOCUMENTS

| | | |
|---|---|---|
| JP | 11-502925 | 3/1999 |
| JP | 2004-502728 A | 1/2004 |
| JP | 2009-539406 A | 11/2009 |
| JP | 2011-520814 A | 7/2011 |
| WO | WO 96/30766 A1 | 10/1996 |
| WO | WO 02/03972 A2 | 1/2002 |
| WO | WO 2007/149293 A2 | 12/2007 |

OTHER PUBLICATIONS

Morris et al, Neuron, 2011, 70:410-26.*
Buèe et al, Brain Res. Rev., 2000, 33:95-130.*
Hiasa et al., Jpn. J. Cancer Res., 1988, 79:314-9.*
Japanese-language Office Action issued in counterpart Japanese Application No. 2014-215409 dated Apr. 20, 2018 with English translation (five (5) pages).
Akoury et al., "Mechanistic Basis of Phenothiazine-Driven Inhibition of Tau Aggregation", Angew. Chem. Int. Ed., 2013, pp. 3511-3515, vol. 52, Wiley-VCH GmbH & Co., Weinheim, Germany.
Walthall et al., "The acute and chronic toxicity of two xanthene dyes, fluorescein sodium salt and phloxine B, to Daphnia pulex", Environmental Pollution, 1999, pp. 207-215, vol. 104, Puyallup Research and Extension Center, Puyallup, Washington.
Akoury, et al., "Mechanistic Basis of Phenothiazine-Driven Inhibition of Tau Aggregation", Angewandte Chemie International Ed., 2013, 52, pp. 1-6, Wiley-VCH Verlag GmbH & Co., KGaA, Weinheim (Six (6) pages).
Crowe, et al., "Aminothienopyridazines and Methylene Blue Affect Tau Fibrillization via Cysteine Oxidation", The Journal of Biological Chemistry vol. 288, No. 16, pp. 11024-11037, Apr. 19, 2013, American Society for Biochemistry and Molecular Biology, Inc., with Supplemental Figure Legends (Nineteen (19) pages).
Yoshiike, et al., "Adaptive responses to alloxan-induced mild oxidative stress ameliorate certain tauopathy phenotypes", Aging Cell, 2012 No. 11, pp. 51-62, Blackwell Publishing Ltd/Anatomical Society of Great Britain and Ireland, with Supplemental Legends for Supporting Figures (Twenty-two (22) pages).
Wittmann, et al., "Tauopathy in *Drosophila*: Neurodegeneration Without Neurofibrillary Tangles", Science vol. 293, pp. 711-714, Jul. 27, 2001, retrieved from www.sciencemag.org with Supplemental Data (Seven (7) pages).
Agarwala et al., 2009, J. Clin Oncology, 27, 15s:9060.
Sarkar, S., Journal of Genetics, vol. 97, No. 3, Jul. 2018, pp. 783-793 (eleven (11) pages).
Japanese-language Office Action issued in counterpart Japanese Application No. 2018-129779 dated Jul. 26, 2019 with English translation (six (6) pages).
Yoshiike Y. et al., "Project Team for Molecular Pathogenesis and Therapeutic Development of Alzheimer's Disease", 2013 Annual Reports, Jun. 4, 2014, National Center for Geriatrics and Gerontology, with partial English Translation (14 pages).

* cited by examiner

*Primary Examiner* — Olga N Chernyshev
(74) *Attorney, Agent, or Firm* — Crowell & Moring LLP

(57) ABSTRACT

The present invention provides a tau protein aggregation inhibitor. In addition, a therapeutic agent or a preventive agent for tauopathy, including a tau protein aggregation inhibitor, and a method for screening for a tau protein aggregation inhibitor, are also provided. The problems are solved by a tau protein aggregation inhibitor including a fluorone dye or a pharmaceutically acceptable salt thereof. Moreover, the problems are also solved by a method for screening a tau protein aggregation inhibitor, wherein the method includes: (1) a step of preparing transgenic *Drosophila* that express a human tau protein in neurons, (2) a step of administering a candidate compound to the transgenic *Drosophila*, and (3) a step of measuring the motor function of the transgenic *Drosophila* that have been administered with the candidate compound in the step (2).

2 Claims, 5 Drawing Sheets

NON-ADMINISTERED    METHYLENE BLUE

NON-ADMINISTERED    METHYLENE BLUE

FIG. 3A
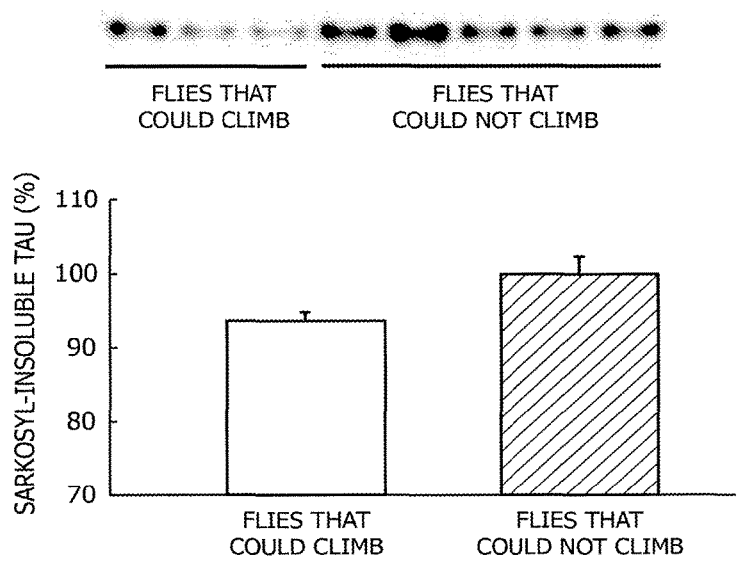
FIG. 3B
FIG. 4A
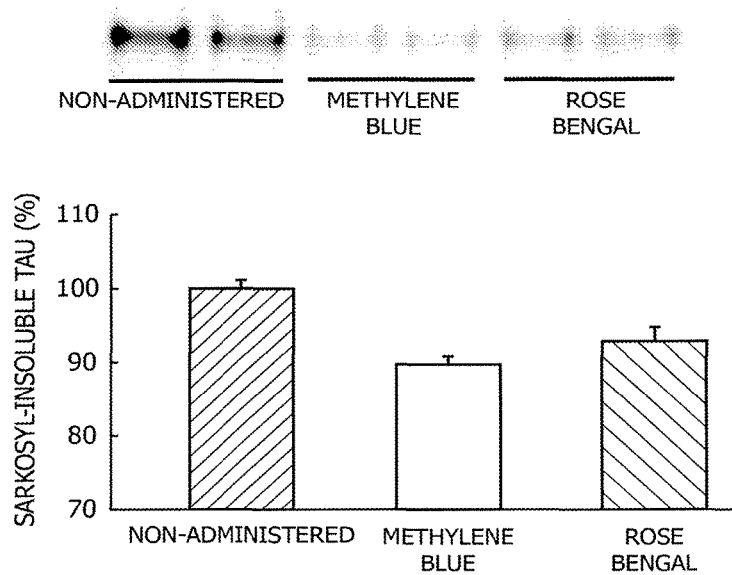
FIG. 4B

THERAPEUTIC AGENT FOR TAUOPATHY AND METHOD FOR SCREENING THEREOF

CROSS-REFERENCE TO RELATED APPLICATION

This application is a divisional of U.S. application Ser. No. 15/111,619 which claims priority from Japanese Patent Application No. 2014-215409 filed Oct. 22, 2014, which is incorporated herein by reference in its entirety.

BACKGROUND OF THE INVENTION

Field of the Invention

The present invention relates to a tau protein aggregation inhibitor. In particular, the present invention relates to a therapeutic agent or a preventive agent for tauopathy, comprising a tau protein aggregation inhibitor, and a method for screening for a tau protein aggregation inhibitor.

Description of Related Art

At present, aging of the Japanese population is progressing at an unprecedented rate, and with such aging of the population, the number of patients with dementia, including Alzheimer's disease as the most common form, has also increased. Currently, the number of patients with dementia in Japan is estimated to be approximately 2,000,000, and it is assumed that the number of the patients will increase with future aging. Since care for such dementia patients is also a large economic burden, it is desired to establish an effective therapeutic method for dementia without any further delay. Currently, for the treatment of Alzheimer's dementia, supportive measures for temporarily ameliorating the symptoms of dementia using a cholinesterase inhibitor, an NMDA inhibitor and the like have been performed. However, the effects of such supportive measures are extremely limited, and thus, it has been strongly desired to establish a fundamental therapeutic method for delaying the onset and progression of Alzheimer's disease.

In order to establish such a fundamental therapeutic method for Alzheimer's disease, the mechanism of onset of Alzheimer's disease needs to be clarified. The following three pathological characteristics, which are commonly observed in Alzheimer's disease patients, have been known: (1) brain shrinkage; (2) formation of macular amyloid accumulations (senile plaques); and (3) formation of fibrous masses in neurons (neurofibrillary tangles (NFT)). In addition, it has been known that formation of senile plaques is caused by aggregation and/or accumulation of amyloid β, and that formation of NFT is caused by aggregation and/or accumulation of tau proteins. Based on these findings, an amyloid hypothesis and a tau hypothesis, in which changes in the conformations of amyloid β and a tau protein cause the onset of Alzheimer's disease, respectively, have been proposed as particularly leading hypotheses.

The tau protein is a microtubule-binding protein existing in a large amount in neurons, mainly in the axons, and it is a protein essential for the function of a nerve axon, which forms cross-linkages between microtubules so as to contribute to promotion and stabilization of the polymerization of microtubules. To date, a plurality of neurodegenerative diseases, in which abnormal accumulation of tau proteins aggregated in neurons is characteristically observed, have been known, and these diseases are collectively referred to as "tauopathies". Tauopathy includes Alzheimer's disease, frontotemporal lobar degeneration, Pick's disease, corticobasal degeneration, progressive supranuclear palsy, and the like. It has been known that all of these diseases exhibit cognitive symptoms. Moreover, abnormal accumulation of tau proteins and the relevant neurodegeneration are observed in familial frontotemporal lobar degeneration (FTDP-17) that is caused by mutation in tau gene, and it has been revealed that a mutation in the tau protein itself is a direct cause of the onset of cognitive symptoms. From these findings, it has been predicted that aggregation and/or abnormal accumulation of tau proteins would be important for all of the mechanisms for development of tauopathies, including Alzheimer's disease. It is anticipated that the search for agents to inhibit aggregation of tau proteins will lead to the development of an agent for fundamental treatment and/or prevention of Alzheimer's disease.

Methylene blue has been reported as a compound having an action to suppress aggregation of tau proteins (Patent Document 1). Methylene blue is a compound having an oxidative activity, and it has been suggested that aggregation of tau proteins is suppressed by oxidative modification of the tau proteins (Non-Patent Documents 1 and 2). Moreover, in recent years, the present inventors have reported that when alloxan, which is a compound having an oxidative activity, is administered to tauopathy model mice, accumulation of tau proteins in the brains is reduced (Non-Patent Document 3). However, since it has been known that alloxan is highly toxic and impairs pancreatic β-cells, it is difficult to use alloxan as a drug. Furthermore, it has also been known that methylene blue is likely to cause chronic toxicity when it is administered for a long period of time, although it is known to be safe for short-term administration (Patent Document 2). Hence, in order to develop an agent for fundamental treatment and/or prevention of Alzheimer's disease, the search for a compound having an action to suppress tau protein aggregation and also having few side effects and high level of safety is extremely important.

A large number of tauopathy model mice have been reported so far, and such tauopathy model mice are extremely useful for examining compounds that become candidates for the drug. However, since a considerable number of mice are required for examining a large number of candidate compounds, the use of such model mice is problematic in that it is extremely expensive and time-consuming. Thus, if *Drosophila*, which have a short life cycle and can be inexpensively and easily bred, were used as model animals, this would be useful for large-scale screening of candidate compounds. However, it has been reported that neurodegeneration is observed in tauopathy model *Drosophila* overexpressing a human tau protein, but formation of NFT cannot be confirmed (Non-Patent Document 4). From this report, it has been suggested that neurodegeneration occurs in *Drosophila* based on a mechanism that is different from the mechanism for formation of NFT. As such, it has been conventionally understood that the *Drosophila* model is not suitable as a system for evaluating aggregation and/or accumulation of tau proteins, and thus that the *Drosophila* model is not adequate for screening for tau protein aggregation inhibitors.

CITATION LIST

Patent Documents

[Patent Document 1] WO 96/30766
[Patent Document 2] WO 02/03972

Non-Patent Documents

[Non-Patent Document 1] Akoury, E. et al., Angew. Chem. Int. Ed. Engl., Vol. 52, pp. 3511-3515 (2013)
[Non-Patent Document 2] Crowe, A. et al., J. Biol. Chem., Vol. 288, pp. 11024-11037 (2013)
[Non-Patent Document 3] Yoshiike, Y. et al., Aging Cell, Vol. 11, pp. 51-62 (2012)
[Non-Patent Document 4] Wittmann, C. W. et al., Science, Vol. 293, pp. 711-714 (2001)

SUMMARY OF THE INVENTION

Problems to be Solved by the Invention

It is an object of the present invention to provide a method for solving various problems of the prior art and for fundamentally preventing and/or treating tauopathies, including Alzheimer's disease.

Means for Solving the Problems

As a result of intensive research, the present inventors have confirmed for the first time that, contrary to conventional findings, aggregation and/or accumulation of tau proteins are observed in Drosophila overexpressing a tau protein. Moreover, the inventor has found for the first time that a correlation is found between the accumulated amount of an aggregated tau protein and the degree of motor dysfunction. Based on these new findings, the present inventors have succeeded in establishing a method for screening for a tau protein aggregation inhibitor using the Drosophila models. Moreover, by applying the aforementioned screening method, they have also found that a fluorone dye is useful as a tau protein aggregation inhibitor.

That is to say, according to one embodiment, the present invention provides a tau protein aggregation inhibitor comprising a fluorone dye or a pharmaceutically acceptable salt thereof.

The fluorone dye is preferably rose bengal.

In addition, according to one embodiment, the present invention provides a therapeutic agent or a preventive agent for tauopathy, comprising the above described tau protein aggregation inhibitor.

The tauopathy is preferably Alzheimer's disease.

Moreover, according to one embodiment, the present invention provides a method for screening for a tau protein aggregation inhibitor, wherein the method comprises: (1) a step of preparing transgenic Drosophila that express a human tau protein in neurons, (2) a step of administering a candidate compound to the transgenic Drosophila, and (3) a step of measuring the motor function of the transgenic Drosophila that have been administered with the candidate compound in the step (2).

The screening method preferably further comprises: (4) a step of measuring the survival rate of the transgenic Drosophila that have been administered with the candidate compound in the step (2).

The screening method preferably further comprises: (5) a step of administering the candidate compound to wild-type Drosophila, and (6) a step of measuring the motor function and/or survival rate of the wild-type Drosophila that have been administered with the candidate compound in the step (5).

The human tau protein is preferably a 2N4R tau isoform.

Effects of the Invention

The tau protein aggregation inhibitor according to the present invention can effectively inhibit aggregation of tau proteins as with methylene blue as a therapeutic agent for Alzheimer's disease, regarding which a phase III clinical trial is currently in progress, and also, the present tau protein aggregation inhibitor has fewer side effects than those of methylene blue and is excellent in terms of safety. Moreover, since the tau protein aggregation inhibitor according to the present invention can ameliorate cognitive symptoms observed in tauopathy by inhibition of aggregation of tau proteins, it becomes possible to provide a method for fundamentally preventing and/or treating tauopathies including Alzheimer's disease as a typical example.

Furthermore, by the method for screening for a tau protein aggregation inhibitor according to the present invention, it becomes possible to carry out prompt and inexpensive high-throughput screening for a large amount of candidate compounds.

BRIEF DESCRIPTION OF THE DRAWINGS

FIGS. 3A and 3B are data demonstrating a correlation between the accumulated amount of an aggregated tau protein and the degree of motor dysfunction in Drosophila expressing a human tau protein specifically in neurons (elav/Y; hTau/+).

FIGS. 4A and 4B are data demonstrating the inhibiting effect on the accumulation of aggregated tau by administering rose bengal to Drosophila expressing a human tau protein specifically in neurons (elav/Y; hTau/+).

DETAILED DESCRIPTION OF THE PREFERRED EMBODIMENTS

Figure 1A:
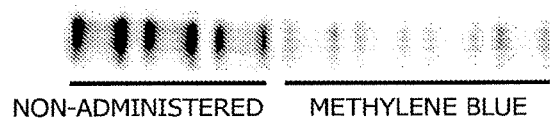
FIGS. 1A and 1B are the results of quantification of the accumulation of aggregated tau in Drosophila expressing a human tau protein specifically in compound eyes (gmr/Y; hTau/+) by immunoblotting.

Hereinafter, the present invention will be described in detail. However, the present invention is not limited to the embodiments described in the present specification.

According to the first embodiment, the present invention relates to a tau protein aggregation inhibitor comprising a fluorone dye or a pharmaceutically acceptable salt thereof.

The "tau protein" (hereinafter also referred to as simply "tau" in the present specification) includes six types of splice variants of wild-type tau expressed from a human tau gene, namely, a 0N3R isoform, a 1N3R isoform, a 2N3R isoform, a 0N4R isoform, a 1N4R isoform and a 2N4R isoform, and the tau protein also includes the variants and homologues of these isoforms, as long as these variants and homologues maintain physiological functions that are equivalent to those of the aforementioned isoforms.

The tau protein aggregation inhibitor of the present embodiment comprises a fluorone dye or a pharmaceutically acceptable salt thereof.

The "fluorone dye" is also referred to an alias "hydroxyxanthene dye," and it is a generic name for xanthene dyes that do not have an amine or a derivative thereof directly binding to a xanthene ring, among xanthene dyes each having a xanthene ring in a molecule thereof (H. J. Conn's Biological stains: a handbook on the nature and uses of the dyes employed in the biological laboratory, Williams & Wilkins, 9th edition, 1977). The fluorone dye used in the present embodiment is not particularly limited, and examples of the fluorone dye include rose bengal (Red No. 105), eosin Y (Red No. 230-(1)), eosin B, ethyl eosin, merbromin (mercurochrome), pyrogallol red, bromopyrogallol red, erythrosine (Red No. 3), phloxine (Red No. 104), fluorescein (Yellow No. 201), uranin (Yellow No. 202-(1)), dibromofluorescein (Orange No. 201), dichlorofluorescein, 4,5,6,7-tetrachlorofluorescein, difluorofluorescein (Oregon Green), fluorescein isothiocyanate (FITC), and carboxyfluorescein. The fluorone dye used in the present embodiment is preferably rose bengal.

The fluorone dye used in the present embodiment can be synthesized by various types of conventionally known chemical synthesis methods. In addition, when the fluorone dye used in the present embodiment is commercially available, such a commercially available product can also be used. Such commercially available products can be purchased, for example, from Sigma-Aldrich, Merck, Tokyo Chemical Industry Co., Ltd., Wako Pure Chemical Industries, Ltd., etc.

The tau protein aggregation inhibitor of the present embodiment encompasses a tau protein aggregation inhibitor comprising a fluorone dye, and a tau protein aggregation inhibitor comprising a pharmaceutically acceptable salt of the fluorone dye.

The term "pharmaceutically acceptable" is used in the present embodiment to mean that it is not harmful upon the use of a drug. Examples of the pharmaceutically acceptable salt used in the present embodiment include: alkaline metal salts such as a sodium salt or a potassium salt; alkaline-earth metal salts such as a magnesium salt or a calcium salt; amine-addition salts such as ammonia, methylamine, dimethylamine, trimethylamine, dicyclohexylamine, tris(hydroxymethyl)aminomethane, ethanolamine, N-methylglucamine, or L-glucamine; and basic amino acid-added salts such as lysine or arginine.

In the present embodiment, a single substance or a mixture consisting of two or more substances selected from the aforementioned fluorone dyes or the pharmaceutically acceptable salts thereof can be used as an active ingredient of the tau protein aggregation inhibitor. The tau protein aggregation inhibitor of the present embodiment may be composed of only the active ingredient. However, in general, the present tau protein aggregation inhibitor may further comprise a pharmaceutically acceptable, known diluent, carrier, excipient, and the like.

In order to produce the tau protein aggregation inhibitor of the present embodiment, the fluorone dye or a pharmaceutically acceptable salt thereof may be formulated optionally in combination with the aforementioned known diluent, carrier, excipient and the like according to a conventional method. The tau protein aggregation inhibitor may comprise, as an active ingredient, the fluorone dye or a pharmaceutically acceptable salt thereof, so that the intake of the active ingredient can be adequate in a range suitable for each dosage form. The content of the fluorone dye or a pharmaceutically acceptable salt thereof in the tau protein aggregation inhibitor is preferably determined, so that the dose can be generally 0.001 mg/kg (body weight) or more, and preferably 0.01 mg/kg (body weight) or more per adult per day. However, the applied dose is not limited to the aforementioned range, and it can be adjusted, as appropriate, depending on the symptoms, age, sex, etc. of a patient. The upper limit of the dose per day is preferably 100 mg/kg (body weight) or less, and more preferably 10 mg/kg (body weight) or less.

The tau protein aggregation inhibitor of the present embodiment can be formulated into various dosage forms. Examples of the dosage form include a tablet, a capsule, a granule, a power agent, syrup, a suspending agent, a suppository, an ointment, a cream, a gelling agent, a patch, an inhalant, and an injection. Accordingly, the tau protein aggregation inhibitor of the present embodiment can be administered by various methods such as oral administration, intraperitoneal administration, intradermal administration, intravenous administration, intramuscular administration, and intracerebral administration.

When the tau protein aggregation inhibitor is formulated into an oral preparation, it can be processed, for example, into a solid agent such as a tablet, a capsule, a power agent or a granule. In this case, suitable additives such as starch, lactose, saccharose, mannitol, carboxymethyl cellulose, corn starch or inorganic salt, and further, as desired, a binder, a disintegrator, a lubricant, a coloring agent, a perfume or the like can be mixed into the tau protein aggregation inhibitor. When such a solid agent is processed into a tablet or a pill, the solid agent may be coated with a sugarcoating substance, or a film of a gastrosoluble or enteric substance, such as sucrose, gelatin or hydroxypropyl cellulose. Alternatively, such an oral preparation of the tau protein aggregation inhibitor can also be processed, for example, into a liquid agent such as syrup, and in this case, sterilized water, normal saline, ethanol or the like can be used as a carrier. Further, an adjuvant such as a suspending agent, a sweetener, a flavoring agent, an antiseptic and the like may also be added to the liquid agent of the tau protein aggregation inhibitor, as desired.

When the tau protein aggregation inhibitor is formulated into a parenteral preparation, it can be processed, for example, into a liquid agent such as an injection or a rectal administration agent. In this case, the active ingredient can be dissolved or suspended in a diluent such as distilled water for injection, normal saline, glucose aqueous solution, vegetable oil for injection, sesame oil, peanut oil, soybean oil, corn oil, propylene glycol or polyethylene glycol according to an ordinary method, and thereafter, a disinfectant, a stabilizer, an isotonicifier, a soothing agent and the like can be added to the obtained solution, as necessary, so as to prepare a parenteral preparation. Alternatively, a solid composition can be produced, and then dissolved in sterilized water or an aseptic injection solvent before use, so that the obtained solution can be used.

Moreover, such a parenteral preparation of the tau protein aggregation inhibitor can also be processed into a sustained release preparation such as a microcapsule, and it can be directly administered into the brain. Such a sustained release preparation can be produced using a carrier capable of preventing immediate removal from a body. Examples of a preferred carrier that can be used herein include biodecomposable/biocompatible polymers such as ethylene vinyl acetate, polyanhydride, polyglycolic acid, collagen, polyorthoester, and polylactic acid. Moreover, a liposome can also be used as a carrier. The type of a preferred liposome is, but not particularly limited to, one prepared by purification according to a reverse phase evaporation method using a lipid composition comprising phosphatidylcholine, cholesterol and a polyethylene glycol-phosphatidylethanolamine (PEG-PE).

Furthermore, the tau protein aggregation inhibitor of the present embodiment may comprise pharmaceutically acceptable additives such as a coloring agent, a preservative, a perfume, a flavoring agent, or a sweetener, or other therapeutic agents, as desired.

Further, upon formulation of the tau protein aggregation inhibitor, it is preferable to mix a stabilizer into the tau protein aggregation inhibitor. Examples of the stabilizer include albumin, globulin, gelatin, mannitol, glucose, dextran, and ethylene glycol.

The amount of the active ingredient contained in a formulation varies depending on various conditions such as the type of an extraction solvent and the amount of a solvent used. Thus, there may be a case in which the amount of the active ingredient is sufficient even if it is smaller than the aforementioned preferred intake, or there may also be a case in which the amount of the active ingredient needs to be larger than the aforementioned range.

The target animals, to which the tau protein aggregation inhibitor of the present embodiment is to be administered, are mammals such as a mouse, a rat, a rabbit, a dog, a bovine, a swine, sheep, a non-human primate and a human, and among these animals, a human is preferable.

Since the tau protein aggregation inhibitor of the present embodiment can suppress aggregation and/or accumulation of tau proteins in brain, it is useful for intended use such as the treatment, prevention, etc. of neurodegenerative diseases associated with such aggregation and/or accumulation of tau proteins. The tau protein aggregation-inhibiting effect of the tau protein aggregation inhibitor of the present embodiment can be confirmed, for example, by administering the present tau protein aggregation inhibitor to a model animal, in which the tau protein has been overexpressed, and biochemically or pathologically analyzing the brain tissues thereof according to known procedures.

According to the second embodiment, the present invention relates to a therapeutic agent or a preventive agent for tauopathy, which comprises the above described tau protein aggregation inhibitor. The therapeutic agent or preventive agent for tauopathy of the present embodiment comprises a tau protein aggregation inhibitor containing a single substance or a mixture of two or more substances selected from the fluorone dyes or the pharmaceutically acceptable salts thereof, and an optional ingredient. The term "an optional ingredient" may be used herein to mean an ordinary ingredient for pharmaceutical products, and the therapeutic agent or preventive agent for tauopathy of the present embodiment may be prepared in commonly used various forms such as a tablet, a capsule, a power agent, a granule, or a liquid agent. In addition, the therapeutic agent or preventive agent for tauopathy according to the present embodiment may further comprise another active ingredient for the treatment or prevention of tauopathy as an optional ingredient.

Among neurodegenerative diseases, the "tauopathy" is a generic name for neurodegenerative diseases in which abnormal accumulation of tau proteins aggregated in neurons is characteristically observed. Examples of the tauopathy include, but are not limited to, Alzheimer's disease, frontotemporal lobar degeneration, Pick's disease, corticobasal degeneration, progressive supranuclear palsy, Down's syndrome, argyrophilic grain dementia, neurofibrillary tangle-predominant dementia, and Parkinson dementia complex.

In the present embodiment, the term "treatment" may be used to mean inhibition or alleviation of progression of the pathologic condition of tauopathy in an animal which has been affected with the tauopathy. The term "treatment" includes not only complete recovery from the disease, but also alleviation of various symptoms of the disease. On the other hand, the term "prevention" is used herein to mean that an animal which is likely to be affected with tauopathy is prevented from being actually affected with the tauopathy.

Tauopathy, which becomes a subject of the therapeutic agent or preventive agent of the present embodiment, is preferably Alzheimer's disease. The "Alzheimer's disease" also includes familial (hereditary) Alzheimer's disease, as well as so-called Alzheimer's disease (sporadic Alzheimer's disease).

The target animals, to which the therapeutic agent or preventive agent for tauopathy of the present embodiment is to be administered, may be mammals such as a mouse, a rat, a rabbit, a dog, a bovine, a swine, sheep, a non-human primate and a human, and among these animals, a human is preferable.

The amount of the fluorone dye or a pharmaceutically acceptable salt thereof added to the therapeutic agent or preventive agent for tauopathy of the present embodiment may be the aforementioned intake depending on the form of a composition. For example, the amount of the fluorone dye or a pharmaceutically acceptable salt thereof is preferably added in the range of 0.0003 to 10% by weight.

The therapeutic agent or preventive agent for tauopathy of the present embodiment can be orally or parenterally administered, and it is preferably orally administered.

Since the therapeutic agent or preventive agent for tauopathy of the present embodiment may inhibit aggregation and accumulation of tau proteins in the brain of a tauopathy patient, it is useful for fundamental treatment or prevention of tauopathy, which targets the mechanism of onset of tauopathy. Moreover, since the therapeutic agent or preventive agent for tauopathy of the present embodiment comprises, as an active ingredient, a fluorone dye such as rose bengal, which can be used as a food additive, it has few side effects and is excellent in terms of safety.

According to a third embodiment, the present invention relates to a method for screening for a tau protein aggregation inhibitor, wherein the method comprises: (1) a step of preparing transgenic *Drosophila* that express a human tau protein in neurons, (2) a step of administering a candidate compound to the transgenic *Drosophila*, and (3) a step of measuring the motor function of the transgenic *Drosophila* that have been administered with the candidate compound in the step (2). According to the screening method of the present embodiment, a compound capable of inhibiting aggregation and/or accumulation of tau proteins can be obtained as a tau protein aggregation inhibitor useful for fundamental treatment or prevention of tauopathy.

In the screening method of the present embodiment, transgenic *Drosophila*, which express a human tau protein in neurons thereof, is produced and is then used. Hereinafter, the transgenic *Drosophila*, which expresses a human tau protein in neurons thereof, is referred to as "*Drosophila* expressing human tau in neurons."

As *Drosophila* expressing human tau in neurons of the present embodiment, any flies of genus *Drosophila* can be used. Among others, *Drosophila melanogaster* is preferably used.

The *Drosophila* expressing human tau in neurons of the present embodiment can be produced using a GAL4-UAS expression system that has been sufficiently established in the present technical field. Specifically, a *Drosophila* strain that expresses a transcriptional factor GAL4 specifically in neurons is mated with a *Drosophila* strain in which a vector including a human tau gene has been introduced downstream of UAS, which is a target sequence of GAL4, so as to produce *Drosophila* expressing human tau in neurons.

With regard to the *Drosophila* strain in which a vector including a human tau gene has been introduced downstream of UAS, the existing strain may be obtained and used. Otherwise, according to a conventionally known method, for example, a transformation vector into which a human tau gene has been incorporated, such as pUAST, may be introduced into the embryo of *Drosophila* to produce a *Drosophila* strain in which a vector including a human tau gene has been introduced downstream of UAS. As a human tau gene, cDNA encoding six types of splice variants of wild-type human tau, namely, a 0N3R tau isoform, a 1N3R tau isoform, a 2N3R tau isoform, a 0N4R tau isoform, a 1N4R tau isoform and a 2N4R tau isoform, may be used. Moreover, cDNA encoding a tau variant that has been known to be associated with tauopathy may also be used. The human tau used in the present embodiment is preferably a 2N4R tau isoform.

When the already existing strain is used as a *Drosophila* strain in which a vector including a human tau gene has been introduced downstream of UAS, examples of an available *Drosophila* strain, into which cDNA encoding a human 2N4R tau isoform has been introduced, include yw:UAS-hTau/TM3 (unpublished, Leo TSUDA, project leader, Animal Models of Aging, National Center for Geriatrics and Gerontology (NCGG)), UAS-hTau, UAS-hTau$^{S2A}$ (S262A/S356A) and UAS-hTau$^{S11A}$ (S46A/T50A/S199A/S202A/S205A/T212A/S214A/T231A/S235A/S396A/S404A) (Chatterjee, S. et al., Hum. Mol. Genet., 18: 164-177 (2009)), UAS-hTau:FLAG and UAS-hTau:STA:FLAG (S238A/T245A) (Kosmidis, S. et al., J. Neurosci., 30: 464-477 (2010)); examples of an available *Drosophila* strain, into which cDNA encoding a human 0N3R tau isoform has been introduced, include UAS-hTau (Williams, D W. et al., J. Comp. Neurol., 428: 630-640 (2000)) and UAS-hTau (Cowan, C M. et al., Acta Neuropathol., 120: 593-604 (2010)); an example of an available *Drosophila* strain, into which cDNA encoding a human 1N4R tau isoform has been introduced, is UAS-hTau (Folwell, J. et al., Exp. Neurol., 223: 401-409 (2010)); examples of an available *Drosophila* strain, into which cDNA encoding a human 0N4R tau isoform has been introduced, include UAS-hTau, UAS-hTau$^{V337M}$ and UAS-hTau$^{R406W}$ (Wittmann, C W. et al., Science, 293: 711-714 (2001)), UAS-hTau$^{R406W/S2A}$ (S262A/S356A) and UAS-hTau$^{R406W/S202A}$ (Nishimura, I. et al., Cell, 116: 671-682 (2004)), UAS-hTau$^{T111A/T153A}$, UAS-hTau$^{T175A/T181A}$, UAS-hTau$^{T199A/T217A}$, UAS-hTau$^{S202A/S205A}$, UAS-hTau$^{T212A}$, UAS-htau$^{S214A}$, UAS-hTau$^{T231A/S235A}$, UAS-hTau$^{S396A/S404A}$, UAS-hTau$^{S422A}$ and UAS-hTau$^{AP5}$ (S202A/S205A/T212A/T231A/S235A) (Steinhilb, M L. et al., Mol. Biol. Cell, 18: 5060-5068 (2007)), UAS-hTau$^{AP}$ (T111A/T153A/T175A/T181A/S199A/S202A/S205A/T212A/S214A/T217A/T231A/S235A/S396A/S404A/S422A) (Steinhilb, M L. et al., J. Neurosci. Res., 85: 1271-1278 (2007)), UAS-hTau$^{S262A}$ (Iijima-Ando, K. et al., Hum. Mol. Genet., 19: 1930-1938 (2010)), UAS-hTau$^{E14}$ (T111E/T153E/T175E/T181E/S199E/S202E/S205E/T212E/T217E/T231E/S235E/S396E/S40 4E/S422E) (Khurana, V. et al., Curr. Biol., 16: 230-241 (2006)); UAS-hTau$^{K44Q/R230Q}$ and UAS-hTau$^{44-230}$ (Reinecke, J B. et al., PLoS ONE, 6: e23865 (2011)), and UAS-hTau$^{1-421}$ (Khurana, V. et al., PLoS Genet., 6: e1001026 (2010)).

With regard to the *Drosophila* strain that expresses GAL4 specifically in neurons, the existing strain may be obtained and used. Otherwise, according to a conventionally known method, a vector, in which a GAL4 gene has been incorporated downstream of a neuron-specific promoter/enhancer, may be introduced into wild-type *Drosophila*, so as to produce such a *Drosophila* strain that neuron-specifically expresses GAL4. The type of such a neuron-specific promoter/enhancer is not particularly limited. For example, elav, App1, R57C10, or the like can be used, and preferably elav can be used.

When the already existing strain is used as a *Drosophila* that expresses GAL4 specifically in neurons, examples of available *Drosophila* strains include: strains expressing GAL4 specifically in neurons, such as elav$^{C155}$-gal4 strain (Lin, D. M. et al., Neuron, 13: 507-523 (1994)), app1-gal4 strain (Torroja, L. et al., Curr. Biol., 9: 489-492 (1999)), and R57C10-gal4 strain (Henry, G L. et al., Nucl. Acids Res., 40: 9691-9704 (2012)); and strains expressing GAL4 in a brain mushroom body neuron-specific manner, such as mb247-gal4 strain (Schulz, R A. et al., Oncogene, 12: 1827-1831 (1996)), 201Y-gal4 strain and c739-gal4 strain (O'Dell, K. M. C. et al., Neuron, 15: 55-61 (1995)); 30Y-gal4 strain and c747-gal4 strain (Yang, M. Y. et al., Neuron, 15: 45-54 (1995)), c309-gal4 strain, OK107-gal4 strain, c772-gal4 strain, c492-gal4 strain and 238y-gal4 strain (Connolly, J. B. et al., Science, 274: 2104-2107 (1996)), NP7175-gal14 strain (Tanaka, N. K. et al., Curr. Biol., 14: 449-457 (2004)), NP6649-gal4 strain, NP3208-gal4 strain, NP3061-gal4 strain, NP1131-gal4 strain, NP65-gal4 strain, and NP2748-gal4 strain (Yoshihara, M. et al., Dros. Inf. Serv., 83: 199-202 (2000)), MZ1489-gal4 strain (Ito, K. et al., Dev. Genes Evol., 204: 284-307 (1995)), 1471-gal4 strain (Isabel, G. et al., Science, 304: 1024-1027 (2004)), H24-gal4 strain and 17d-gal4 strain (Martin, J. R. et al., Learn. Mem., 5: 179-191 (1998)), D52H-gal4 strain (Qiu, Y. et al., Genes Dev., 7: 1447-1458 (1993)), c320-gal4 strain (Krashes, M. J. et al., J. Neurosci., 28: 3103-3113 (2008)), and 103y-gal4 strain (Tettamanti, M. et al., Dev. Genes Evol., 207: 242-252 (1997)).

The above described *Drosophila* strains are available from domestic or international public stock centers such as the KYOTO Stock Center, Department of *Drosophila* Genomics and Genetic Resources (http://www.dgrc.kit.ac.jp/), or Bloomington *Drosophila* Stock Center at Indiana University (http://flystocks.bio.indiana.edu/).

The *Drosophila* expressing human tau in neurons of the present embodiment express human tau in the neurons thereof, and the aggregated tau is then accumulated in the brain thereof. The accumulation of the aggregated tau can be confirmed by detecting tau proteins present in a sarkosyl-insoluble fraction extracted from the brain tissues of the *Drosophila*, and then quantifying them. Detection and quantification of such a sarkosyl-insoluble tau can be carried out, for example, by immunoblotting using an anti-human tau antibody.

Subsequently, a candidate compound is administered to the *Drosophila* expressing human tau in neurons. Examples of such a candidate compound include a synthetic compound, a peptidic compound, a nucleic acid, and an antibody. These candidate compounds may be either novel compounds or known compounds.

In order to administer such a candidate compound to Drosophila, candidate compounds having various concentrations may be added to food, and the Drosophila may be then fed with the food. The concentration of the candidate compound added to the food may be different depending on the type of the compound. For example, the concentration can be selected, as appropriate, from the range of 0.1 mM to 100 mM. The candidate compound can be administered, for example, over 1 minute to 6 months.

Subsequently, the transgenic Drosophila, to which the candidate compound has been administered, is measured in terms of motor function. Since the motor function of the human tau-expressing Drosophila of the present embodiment is reduced in correlation with the accumulated amount of aggregated tau in the brain tissues, the accumulation level of aggregated tau in the brain tissues can be evaluated by measuring the motor function. The motor function can be measured by evaluating negative gravitaxis (negative geotaxis), for example, according to climbing assay that is a method sufficiently established in the present technical field. Since the motor function can be measured only by visual observation of the movement of Drosophila, it is possible to evaluate the accumulation level of aggregated tau in the brain tissues of the Drosophila, much more easily and promptly than a method which comprises extracting sarkosyl-insoluble tau from the brain tissues and quantifying it.

In order to determine whether the motor function of the transgenic Drosophila, to which the candidate compound has been administered, has been improved or reduced, the motor function of transgenic Drosophila, to which the candidate compound has not been administered, may also be measured at the same time, and the results of the two measurements may be then compared. Alternatively, the measurement value of the motor function of the transgenic Drosophila, to which the candidate compound has been administered, may be compared with the previously measured value of the motor function of the transgenic Drosophila, to which the candidate compound had not been administered.

In the screening method of the present embodiment, when the motor function of the transgenic Drosophila, to which the candidate compound has been administered, is significantly improved in comparison to the motor function of the transgenic Drosophila, to which the candidate compound has not been administered, it is understood that the accumulated amount of aggregated tau has been reduced in the brain tissues of the Drosophila, so that this candidate compound can be evaluated to be promising as a tau protein aggregation inhibitor. On the other hand, when the motor function of the transgenic Drosophila, to which the candidate compound has been administered, is not changed or is reduced in comparison to the motor function of the transgenic Drosophila, to which the candidate compound has not been administered, it is understood that the accumulated amount of aggregated tau has not been reduced in the brain tissues of the Drosophila, so that it can be evaluated that this candidate compound is not promising as a tau protein aggregation inhibitor.

The screening method of the present embodiment may further comprise: (4) a step of measuring the survival rate of the transgenic Drosophila that have been administered with the candidate compound in the step (2). The toxicity of the candidate compound can be evaluated by confirming the influence of the candidate compound on the survival rate of the transgenic Drosophila. The step (4) is preferably performed on candidate compounds, which have been evaluated to be promising as tau protein aggregation inhibitors based on the results of the steps (1) to (3).

In order to determine whether the survival rate of the transgenic Drosophila, to which a candidate compound has been administered, has been improved or reduced, the survival rate of transgenic Drosophila, to which the candidate compound has not been administered, may also be measured at the same time, and the results of the two measurements may be then compared. Alternatively, the measurement value of the survival rate of the transgenic Drosophila, to which the candidate compound has been administered, may be compared with the previously measured value of the survival rate of the transgenic Drosophila, to which the candidate compound had not been administered.

In the screening method of the present embodiment, when the survival rate of the transgenic Drosophila, to which the candidate compound has been administered, is not changed or is improved in comparison to the survival rate of the transgenic Drosophila, to which the candidate compound has not been administered, it is understood that the toxicity of the candidate compound is low, so that the candidate compound can be evaluated to be promising as a tau protein aggregation inhibitor used for the treatment or prevention of tauopathy. On the other hand, when the survival rate of the transgenic Drosophila, to which the candidate compound has been administered, is reduced in comparison to the survival rate of the transgenic Drosophila, to which the candidate compound has not been administered, it is understood that the toxicity of the candidate compound is high, so that it can be evaluated that the candidate compound is not suitable as a tau protein aggregation inhibitor used for the treatment or prevention of tauopathy, even if it has an excellent protein aggregation-inhibiting effect.

The screening method of the present embodiment may further comprise: (5) a step of administering the candidate compound to wild-type Drosophila, and (6) a step of measuring the motor function and/or survival rate of the wild-type Drosophila that have been administered with the candidate compound in the step (5). The steps (5) and (6) can be preferably performed on candidate compounds, which have been evaluated to be promising as tau protein aggregation inhibitors based on the results of the steps (1) to (3). These steps can be particularly preferably performed on candidate compounds, which have been evaluated to be promising as tau protein aggregation inhibitors based on the results of the steps (1) to (4). The toxicity of the candidate compound can be accurately evaluated by confirming the influence of the candidate compound on the motor function and survival rate of wild-type Drosophila. It is to be noted that the numbers 1 to 6 of the steps (1) to (6) are not intended to limit the order of performing individual steps, and thus that the step (4) may be carried out, for example, after completion of the steps (5) and (6).

In order to determine whether the motor function and/or survival rate of wild-type Drosophila, to which a candidate compound has been administered, have been improved or reduced, the motor function and/or survival rate of wild-type Drosophila, to which the candidate compound has not been administered, may be measured at the same time, and the obtained results may be then compared with each other. Alternatively, the measurement values of the motor function and/or survival rate of wild-type Drosophila, to which the candidate compound has been administered, may be compared with the previously measured values of the motor function and/or survival rate of wild-type *Drosophila*, to which the candidate compound has not been administered.

In the screening method of the present embodiment, when the motor function and/or survival rate of the wild-type *Drosophila*, to which the candidate compound has been administered, are not changed or are improved in comparison to the motor function and/or survival rate of the wild-type *Drosophila*, to which the candidate compound has not been administered, it is understood that the toxicity of the candidate compound is low, so that the candidate compound can be evaluated to be promising as a tau protein aggregation inhibitor used for the treatment or prevention of tauopathy. On the other hand, when the motor function and/or survival rate of the wild-type *Drosophila*, to which the candidate compound has been administered, are reduced in comparison to the motor function and/or survival rate of the wild-type *Drosophila*, to which the candidate compound has not been administered, it is understood that the toxicity of the candidate compound is high, so that it can be evaluated whether the candidate compound is or is not suitable as a tau protein aggregation inhibitor used for the treatment or prevention of tauopathy, even if it has an excellent protein aggregation-inhibiting effect.

EXAMPLES

Hereinafter, the present invention will be more specifically described in the following examples. However, these examples are not intended to limit the scope of the present invention.

1. Materials and Methods (1) Production of Human tau-Expressing *Drosophila* and Breeding Thereof Transgenic *Drosophila* expressing a human tau protein specifically in compound eyes, transgenic *Drosophila* expressing a human tau protein specifically in neurons, and transgenic *Drosophila* expressing a human tau protein specifically in brain mushroom body neurons were produced using a GAL4-UAS expression system. As a UAS-hTau strain in which a human tau gene (hTau) had been inserted downstream of a GAL4-binding enhancer sequence (UAS), yw:UAS-hTau/TM3 (unpublished; furnished by Leo TSUDA, project leader, Animal Models of Aging, National Center for Geriatrics and Gerontology (NCGG)) was used. As a *Drosophila* strain expressing GAL4 specifically in compound eyes, a gmr-gal4 strain (Hay, B A. et al., Development, 120: 2121-2129 (1994); furnished by Leo TSUDA, project leader, Animal Models of Aging, National Center for Geriatrics and Gerontology (NCGG)) was used. As a *Drosophila* strain expressing GAL4 specifically in neurons, an elav$^C$155gal4 strain (Lin, D. M. et al., Neuron, 13: 507-523 (1994); furnished by Leo TSUDA, project leader, Animal Models of Aging, National Center for Geriatrics and Gerontology (NCGG)) was used. As a *Drosophila* strain expressing GAL4 specifically in brain mushroom body neurons, an mb247-gal4 strain (Schulz, R A. et al., Oncogene, 12: 1827-1831 (1996); furnished by Leo TSUDA, project leader, Animal Models of Aging, National Center for Geriatrics and Gerontology (NCGG)) was used. The UAS-hTau strain was mated with each of the above described tissue-specific gal4 strains to obtain F1 progenies, namely, *Drosophila* expressing human tau in compound eyes (gmr/Y; hTau/+), *Drosophila* expressing human tau in neurons (elav/Y; hTau/+), and *Drosophila* expressing human tau in mushroom body neurons (mb/Y; hTau/+).

Male F1 *Drosophila* one to three days after emergence were bred under an environment consisting of a temperature of 25±3° C., a humidity of 60±10%, and a light-dark cycle of 12 hours. During the breeding, normal food was given to a non-administration group, whereas food, to which methylene blue (manufactured by Wako Pure Chemical Industries, Ltd.) or rose bengal (manufactured by Wako Pure Chemical Industries, Ltd.) each having a final concentration of 1 mM had been added, was given to a methylene blue administration group or a rose bengal administration group. The flies were transferred into a vial filled with fresh food once every two weeks. Based on the assumption that a fly ingests 1.5 µL of food, to which methylene blue with a final concentration of 1 mM has been added, every day (i.e., the fly ingests 480 ng/day methylene blue) (Ja, W W. et al., Proc. Nat. Acad. Sci. USA., 104: 8253-8256 (2007)), with respect to a fly that is 2 mm in height and 0.5 mg in body weight, the amount of methylene blue ingested by a human (body: 60 kg, Km value=37) is estimated to be approximately 150 mg/day (for this conversion method, see Mosteller, R D., N. Engl. J. Med., 317: 1098 (1987) and Reagan-Shaw, S. et al., FASEB J., 22: 659-661 (2008)). This dose is almost equivalent to the dose of methylene blue applied in the phase III clinical trial (150 to 250 mg/day).

(2) Quantification of Aggregated tau

The flies, which had been bred for 1 month under the conditions described in (1) above, were decapitated under anesthesia with carbon dioxide, and the heads were then recovered under cooling on ice to result in approximately 20 fly heads/1.5 mL tube. Thereafter, the recovered heads were cryopreserved at −80° C. A TBS buffer (10 mM Tris, 150 mM NaCl (pH 7.4), 1 mM EDTA, 1 mM EGTA) was added to each tube (5 µL/head). Thereafter, the obtained mixture was homogenized and was then ultracentrifuged (24,000 g, 20 minutes, 2° C.), and the obtained supernatant was recovered in another tube. This supernatant was mixed with a sample buffer (120 mM Tris (pH 6.8), 10% 2-mercaptoethanol, 4% SDS, 20% glycerol, 0.02% bromophenol blue), and the obtained solution was defined as a TBS-soluble fraction sample. On the other hand, to a pellet from which the supernatant had been removed, sucrose-containing TBS (10 mM Tris, 800 mM NaCl (pH 7.4), 1 mM EGTA, 10% sucrose) was added, and the obtained mixture was homogenized again and was then ultracentrifuged (24,000 g, 20 minutes, 2° C.). The obtained supernatant was recovered in another ultracentrifuge tube. To this supernatant, sarkosyl (final concentration: 1% (w/v)) was added, and the obtained mixture was then incubated at a room temperature for 3 hours. Thereafter, the reaction solution was ultracentrifuged (420,000 g, 1 hour, 4° C.), and a sample buffer was then added to and suspended in a pellet obtained by removing the supernatant. The thus obtained solution was defined as a sarkosyl-insoluble fraction sample. A tau protein is separated into a TBS-soluble fraction when it is not aggregated, whereas it is separated into a sarkosyl-insoluble fraction when it is aggregated and insolubilized.

The TBS-soluble fraction sample and the sarkosyl-insoluble fraction sample were each subjected to SDS-PAGE. The fractions were each electrophoresed, and were then transcribed on a nitrocellulose membrane, followed by performing immunoblotting, so that tau was detected in each sample and was then quantified. Tau in the TBS-soluble fraction sample was subjected to immunoblotting, using an anti-tau antibody (taus, manufactured by Life Technologies, 1:1000) as a primary antibody, and using an anti-mouse antibody (Peroxidase-conjugated AffiniPure Donkey Anti-Mouse IgG (H+L), manufactured by Jackson Immuno Research Laboratories, 1:1000) as a secondary antibody. Detection was carried out using Novex ECL HRP Chemiluminescent Substrate Reagent Kit (manufactured by Life Technologies). Tau in the sarkosyl-insoluble fraction sample was subjected to immunoblotting, using an anti-tau antibody (JM antibody, Takashima, A. et al., Proc. Natl. Acad. Sci. USA., 1998, 95 (16): 9637-9641; furnished by Akihiko TAKASHIMA, department director, Department of Aging Neurobiology, National Center for Geriatrics and Gerontology (NCGG); 1:1000) as a primary antibody, and using an anti-rabbit antibody (Peroxidase-conjugated AffiniPure Donkey Anti-Rabbit IgG (H+L), manufactured by Jackson Immuno Research Laboratories, 1:1000) as a second antibody. Detection was carried out using ImmunoStar LD (manufactured by Wako Pure Chemical Industries, Ltd.). The detected band was quantified using image analysis software (ImageJ 1.36 b, manufactured by U.S. National Institutes of Health), and the amount of tau in each group was subjected to comparative quantification.

(3) Measurement of Motor Function

The motor function of *Drosophila* of was measured by performing climbing assay and evaluating negative gravitaxis. The climbing assay was carried out under the following conditions. *Drosophila* was transferred into an empty vial containing no food, and the vial was then hit, so that flies fell to the bottom. Thereafter, the movement of the flies climbing up the wall was captured on video. The flies, which were below the line drawn at the position 3 cm from the bottom 10 seconds after they had fallen to the bottom, were defined as "flies that could not climb", and flies, which were above the aforementioned line, were defined as "flies that could climb". The number of flies of each type was counted. The total number of flies in the vial was set at 100%, and the percentage of the flies that could climb was calculated.

(4) Calculation of Survival Rate

*Drosophila* were bred under the conditions described in (1) above, and the number of surviving flies was counted every three days, and the survival rate was then calculated.

(5) Analysis of Olfactory Memory

As a memory test of *Drosophila*, a discrimination learning test with odor and electric shock was carried out. Using two types of odor substances (3-octanol and 4-methylcyclohexanol), which *Drosophila* dislikes, and flies were allowed to sniff either one odor (Odor 1) for 1 minute, while electric shock (60 V of pulse current with intervals of 5 seconds) was given thereto. After 45-second break, the flies were allowed to sniff the other odor (Odor 2) for 1 minute, without giving electric shock thereto. Thereby, the flies learned the firstly sniffed Odor 1 as a harmful odor. After completion of the learning for 1 minute 30 seconds, both a vessel containing Odor 1 and a vessel containing Odor 2 were simultaneously given to the flies, and which odor the flies selected was observed. The flies were placed between the vessel containing Odor 1 and the vessel containing Odor 2, and the memory score obtained when the number of flies transferred to the vessel containing Odor 1 and the number of flies transferred to the vessel containing Odor 2 were equal to each other was defined as 0%, and the memory score when all of the flies transferred to the vessel containing Odor 2 was defined as 100%. Thereafter, the combination of odor and electric shock was exchanged, and the same test as described above was then carried out. A mean value was obtained from the obtained result and the result of the first test, and this value was used as a single test result.

2. Accumulation of Aggregated tau in *Drosophila* Expressing Human tau in Compound Eyes Thereof The accumulation of aggregated tau in the *Drosophila* expressing human tau in the compound eyes thereof (gmr/Y; hTau/+) produced in (1) above was quantified by the procedures in (2) above. Quantification of the aggregated tau was carried out on a non-administration group and a methylene blue administration group. The accumulation of aggregated tau in both groups was subjected to comparative quantification, setting the numerical value of the non-administration group at 100%.

Figure 1B:
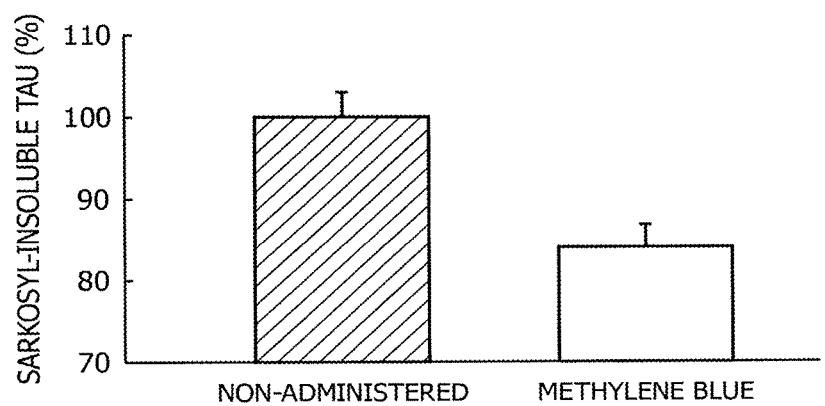
Figure 2A:
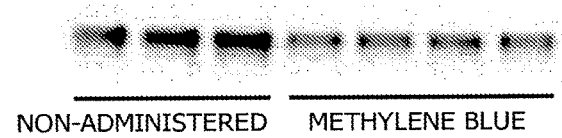
FIGS. 2A and 2B are the results of quantification of the accumulation of soluble tau in Drosophila expressing a human tau protein specifically in compound eyes (gmr/Y; hTau/+) by immunoblotting.
Figure 2B:
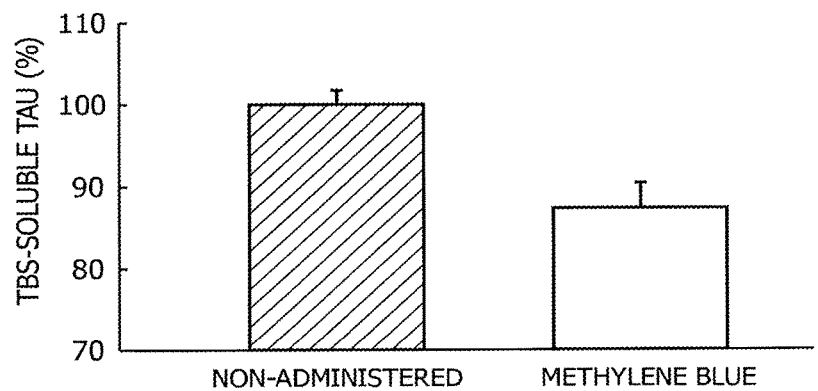

The results are shown in FIG. 1 and FIG. 2. In the sample prepared from the non-administration group, strong signals were observed not only in the TBS-soluble fraction, but also in the sarkosyl-insoluble fraction (FIG. 1(*a*) and FIG. 2(*a*)). From these results, it was confirmed that the accumulation of aggregated tau occurs as a result of the overexpression of human tau in *Drosophila*. In addition, it was demonstrated that, in the sample prepared from the methylene blue administration group, the accumulation of aggregated tau is significantly reduced (FIG. 1(*b*)). It has been known that methylene blue has an action to suppress tau aggregation, and at present, the phase III clinical trial is in progress on methylene blue as a therapeutic agent for Alzheimer's disease, using tau as a target. From the aforementioned results, it was demonstrated that tau aggregation in *Drosophila* can be suppressed by administration of methylene blue. Thus, it was suggested that *Drosophila* overexpressing human tau can be animal models for evaluating tau aggregation.

3. Establishment of Screening System for tau Protein Aggregation Inhibitor, Using *Drosophila* Expressing Human tau in Neurons Next, the *Drosophila* expressing human tau in the neurons thereof (elav/Y; hTau/+) produced in (1) above was evaluated in terms of motor function according to the procedures in (3) above. Thereafter, a fly group that had climbed and a fly group that had not climbed were recovered, and each group was quantified in terms of the accumulation of aggregated tau in brain according to the procedures in (2) above. The accumulated amount of aggregated tau in both groups was subjected to comparative quantification, setting the numerical value of the fly group that had not climbed to the top at 100%.

The results are shown in FIG. 3. It was confirmed that in the flies that could not climb, the accumulated amount of aggregated tau in brain was larger than that in the flies that could climb. From these results, it was demonstrated that the motor function of *Drosophila* is reduced in correlation with the accumulated amount of aggregated tau in brain.

Hence, it was confirmed for the first time that aggregation and/or accumulation of tau are observed in the brain of *Drosophila* overexpressing human tau, and that there is a correlation between the accumulated amount of aggregated tau and the degree of motor dysfunction. From these results, it was demonstrated that it is possible to screen for a tau protein aggregation inhibitor by measuring the motor function of *Drosophila* overexpressing human tau in neurons.

4. Screening for tau Protein Aggregation Inhibitor Using *Drosophila* Expressing Human tau in Neurons Using the screening system established in 3 above, the tau protein aggregation-inhibiting effect of rose bengal, which is a fluorone dye, was evaluated. Using the *Drosophila* expressing human tau in the neurons thereof (elav/Y; hTau/+) produced in (1) above, a rose bengal administration group, a non-administration group (negative control), and a methylene blue administration group (positive control) were prepared. Thereafter, the accumulation of aggregated tau in brain was quantified according to the procedures in (2) above. The accumulated amount of aggregated tau in individual groups was subjected to comparative quantification, setting the numerical value of the non-administration group at 100%. In addition, the aforementioned individual groups were measured in terms of motor function according to the procedures in (3) above.

Figure 5:
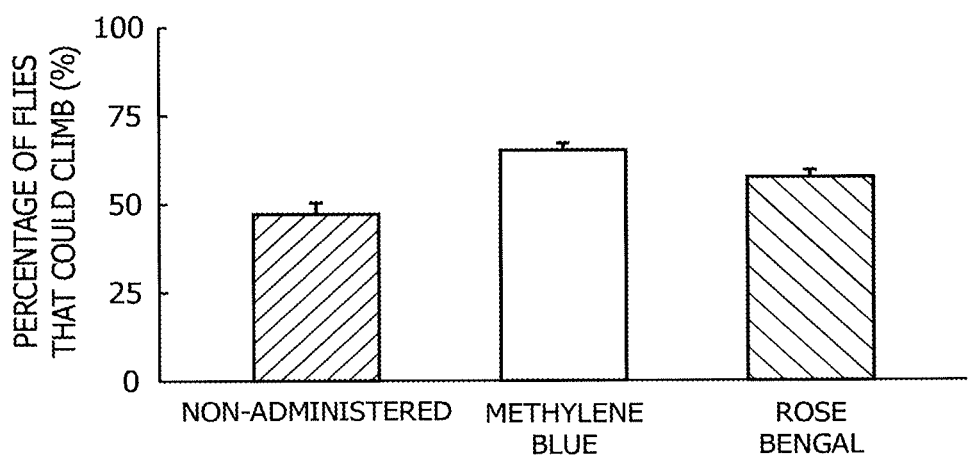
FIG. 5 is data demonstrating the improving effect on the motor function by administering rose bengal to Drosophila expressing a human tau protein specifically in neurons (elav/Y; hTau/+).

The results are shown in FIG. 4 and FIG. 5. As in the case of the methylene blue administration group, a reduction in the accumulated amount of aggregated tau in brain was confirmed in the rose bengal administration group (FIG. 4). Moreover, as in the case of the methylene blue administration group, it was confirmed that motor function was recovered in the rose bengal administration group (FIG. 5). From these results, it was suggested that rose bengal has the same tau protein aggregation-inhibiting effect as that of methylene blue, and thus that rose bengal can be used as a tau protein aggregation inhibitor.

5. Evaluation of Toxicity of Rose Bengal

While methylene blue has a tau aggregation-suppressing action, there are concerns about the chronic toxicity of methylene blue caused by long-term administration. Thus, rose bengal or methylene blue was administered to *Drosophila* expressing human tau in the neurons thereof or wild-type *Drosophila*, the survival rate of each type of *Drosophila* was then calculated according to the procedures in (4) above, and the results were then compared with one another, so as to evaluate the toxicity of rose bengal. As a control, the *Drosophila* in the non-administration group was used.

Figure 6:
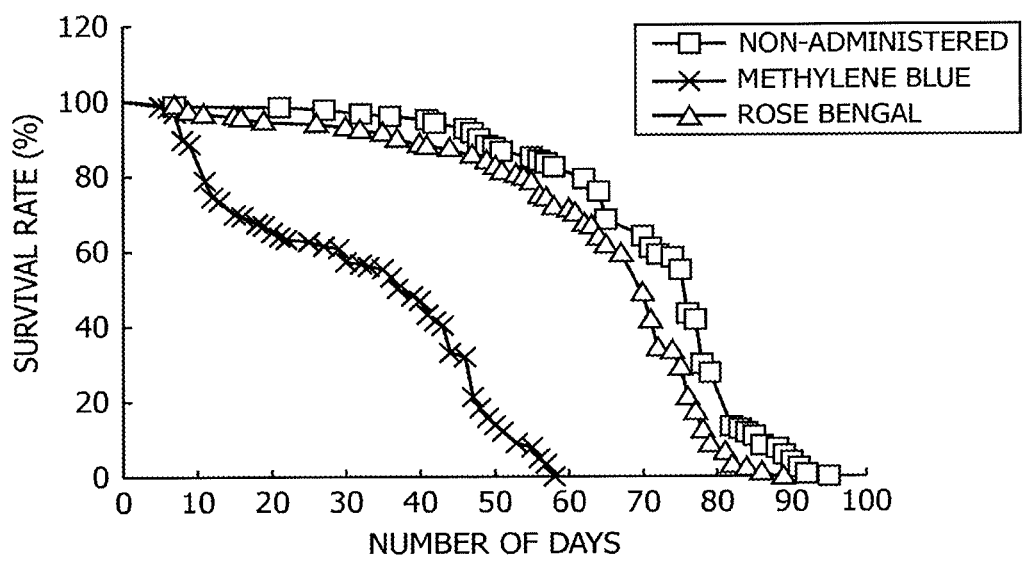
FIG. 6 is data demonstrating the survival rate of Drosophila expressing a human tau protein specifically in neurons (elav/Y; hTau/+), when rose bengal is administered thereto.
Figure 7:
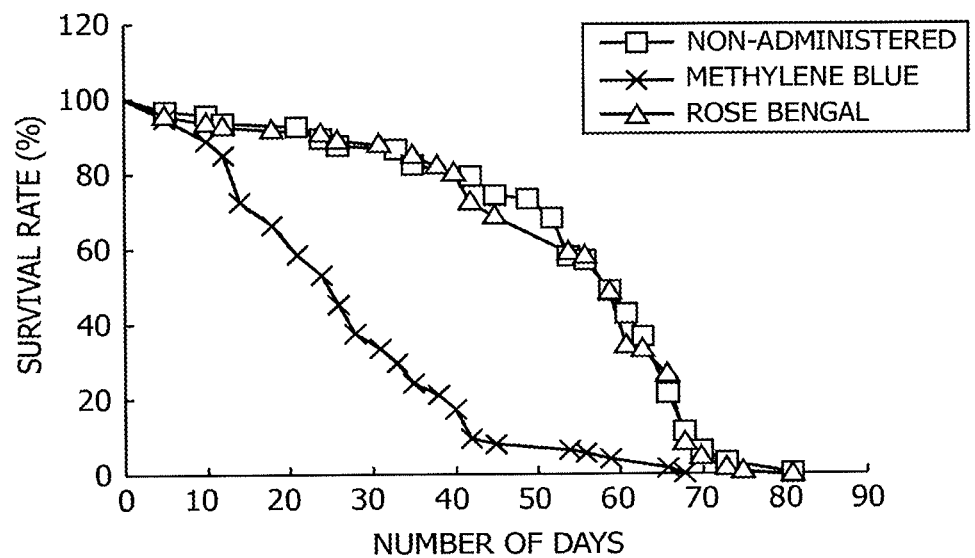
FIG. 7 is data demonstrating the survival rate of wild-type Drosophila, when rose bengal is administered thereto.

The results are shown in FIG. 6 and FIG. 7. When methylene blue was administered, survival rate was significantly reduced both in the *Drosophila* expressing human tau in the neurons thereof and in the wild-type *Drosophila*. In contrast, when rose bengal was administered, the survival rate of the *Drosophila* expressing human tau in the neurons thereof was almost equivalent to the survival rate of the *Drosophila* in the non-administration group (FIG. 6). On the other hand, it was revealed that no significant change is observed in the survival rate of the wild-type *Drosophila* by administration of rose bengal (FIG. 7). From these results, it was demonstrated that rose bengal is a tau protein aggregation inhibitor having toxicity lower than that of methylene blue.

Furthermore, using wild-type *Drosophila*, a non-administration group, a methylene blue administration group and a rose bengal administration group were prepared, and these groups were then measured in terms of motor function according to the procedures in (3) above.

Figure 8:
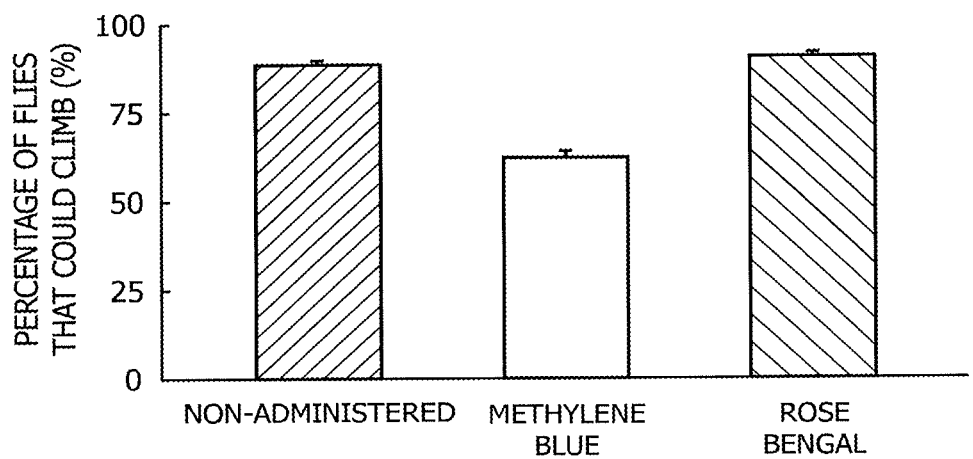
FIG. 8 is data demonstrating the motor function of wild-type Drosophila, when rose bengal is administered thereto.

The results are shown in FIG. 8. In the methylene blue administration group, the percentage of the flies that had climbed above the line was significantly reduced, whereas in the rose bengal administration group, the percentage of the flies that had climbed above the line was not reduced at all. Also from these results, it was demonstrated that rose bengal has lower toxicity and fewer side effects than methylene blue.

From the aforementioned results, it was understood that rose bengal has lower toxicity and fewer side effects than methylene blue, and it was suggested that such rose bengal would be a tau protein aggregation inhibitor suitable for the development of clinical pharmaceuticals.

6. Improvement of Olfactory Memory by Administration of Rose Bengal

Whether the learning and memory ability of human tau-expressing *Drosophila* is changed when rose bengal is administered to the *Drosophila* to inhibit tau aggregation was examined according to the procedures in (5) above, using the *Drosophila* expressing human tau in the mushroom body neurons thereof (mb/Y; hTau/+) produced in (1) above. Rose bengal was administered to the *Drosophila* over 1 week. In addition, as controls, wild-type *Drosophila* non-administration group and wild-type *Drosophila* rose bengal administration group were produced, and were subjected to the same test as described above.

Figure 9:
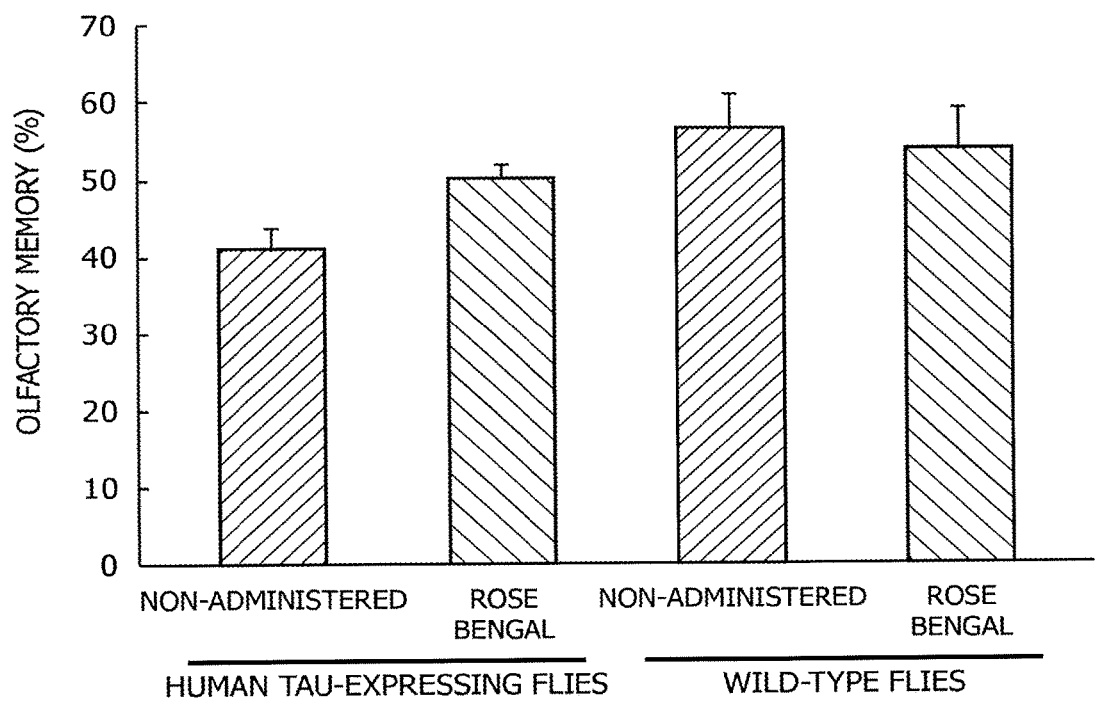
FIG. 9 is data demonstrating the improving effect on the olfactory memory by administering rose bengal to Drosophila expressing a human tau protein specifically in neurons in the mushroom body of the brain (mb/Y; hTau/+).

The results are shown in FIG. 9. The *Drosophila* expressing human tau in the mushroom body neurons thereof exhibited significantly low olfactory memory, in compared to the wild-type *Drosophila*. However, when rose bengal was administered to the *Drosophila* expressing human tau in the mushroom body neurons thereof, such olfactory memory was significantly improved. On the other hand, in the case of the wild-type *Drosophila*, no significant change was observed in olfactory memory between the non-administration group and the rose bengal administration group. From these results, it was understood that rose bengal can inhibit the accumulation of aggregated tau to improve the memory ability of the *Drosophila* expressing human tau in the mushroom body neurons thereof, and it was suggested that rose bengal would be useful as a therapeutic agent for tauopathies such as Alzheimer's disease.

As such, it was demonstrated that fluorone dyes including rose bengal can inhibit abnormal accumulation of aggregated tau proteins, which is a mechanism for onset of tauopathies including Alzheimer's disease, can also ameliorate cognitive symptoms observed in tauopathies, and also has few side effects and high level of safety, so that the fluorone dyes including rose bengal are useful for the development of fundamentally therapeutic agent and/or preventive agent for tauopathies.

The invention claimed is:

1. A method for inhibiting aggregation of tau proteins in *Drosophila* expressing human tau protein in neurons, comprising contacting the tau proteins with a fluorone dye or a pharmaceutically acceptable salt thereof, wherein aggregation of tau proteins is less in the presence of a fluorone dye as compared to tau aggregation in the absence of a fluorone dye.

2. The method according to claim 1, wherein the fluorone dye is rose bengal.

* * * * *